United States Patent [19]

Iwasa et al.

[11] Patent Number: 5,175,268
[45] Date of Patent: Dec. 29, 1992

[54] DNA ENCODING RECOMBINANT HUMAN LYMPHOTOXIN

[75] Inventors: Susumu Iwasa, Tsuzuki; Tomoko Fujii, Toyonaka; Ryuji Marumoto, Ashiya; Koichi Igarashi, Kyoto, all of Japan

[73] Assignee: Takeda Chemical Industries, Ltd., Osaka, Japan

[21] Appl. No.: 416,657

[22] Filed: Oct. 3, 1989

Related U.S. Application Data

[62] Division of Ser. No. 136,029, Dec. 21, 1987, abandoned.

[30] Foreign Application Priority Data

Dec. 24, 1986 [JP] Japan ................................. 61-306385

[51] Int. Cl.$^5$ ....................... C07H 21/04; C12N 15/19
[52] U.S. Cl. .................................. 536/27; 536/28; 536/29; 530/351
[58] Field of Search .................................. 536/27–29

[56] References Cited

U.S. PATENT DOCUMENTS

| | | | |
|---|---|---|---|
| 4,677,063 | 6/1987 | Mark et al. | 435/68 |
| 4,677,064 | 6/1987 | Mark et al. | 435/68 |
| 4,782,139 | 11/1988 | DiMarchi et al. | 530/407 |

FOREIGN PATENT DOCUMENTS

| | | |
|---|---|---|
| 164965 | 12/1985 | European Pat. Off. |
| 207518 | 1/1987 | European Pat. Off. |
| 0230781 | 8/1987 | European Pat. Off. |
| 232107 | 8/1987 | European Pat. Off. |
| 62-151182 | 7/1987 | Japan |
| 62-282583 | 12/1987 | Japan |

OTHER PUBLICATIONS

Kobayashi et al., Journal of Biochemistry, vol. 100, No. 3, 727–733 (Sep. 1986).
Aggarwall et al., J. Biol. Chem., 259: 686 (1984).
Gray et al., Nature 312: 721 (1984).
Pennica et al., Nature 312: 724, (1984).
Aggarwal et al., J. Biol. Chem. 260: 2334 (1985).

Primary Examiner—Johnnie R. Brown
Assistant Examiner—L. Eric Crane
Attorney, Agent, or Firm—David G. Conlin; Ronald I. Eisenstein

[57] ABSTRACT

Lymphotoxin (LT) mutein (genetically-altered LT) is disclosed that has the following amino acid sequence, or a portion of an active portion of said protein, where 10 to 21 amino acids of LT being deleted from N-terminus and which has Pro or Phe at the N-terminus:

H—(Met)n—R$_1$—R$_2$—Ala—His—Ser—Thr—Leu—Lys—Pro—Ala—
  Ala—His—Leu—Ile—Gly—Asp—Pro—Ser—Lys—
  Gln—Asn—Ser—Leu—Leu—Trp—Arg—Ala—Asn—
  Thr—Asp—Arg—Ala—Phe—Leu—Gln—Asp—Gly—
  Phe—Ser—Leu—Ser—Asn—Asn—Ser—Leu—Leu—
  Val—Pro—Thr—Ser—Gly—Ile—Tyr—Phe—Val—
  Tyr—Ser—Gln—Val—Val—Phe—Ser—Gly—Lys—
  Ala—Tyr—Ser—Pro—Lys—Ala—Thr—Ser—Ser—
  Pro—Leu—Tyr—Leu—Ala—His—Glu—Val—Gln—
  Leu—Phe—Ser—Ser—Gln—Tyr—Pro—Phe—His—
  Val—Pro—Leu—Leu—Ser—Ser—Gln—Lys—Met—
  Val—Tyr—Pro—Gly—Leu—Gln—Glu—Pro—Trp—
  Leu—His—Ser—Met—Tyr—His—Gly—Ala—Ala—
  Phe—Gln—Leu—Thr—Gln—Gly—Asp—Gln—Leu—
  Ser—Thr—His—Thr—Asp—Gly—Ile—Pro—His—
  Leu—Val—Leu—Ser—Pro—Ser—Thr—Val—Phe—
  Phe—Gly—Ala—Phe—Ala—Leu—OH

Wherein R$_1$ is Pro or Phe, R$_2$ is a peptide chain represented by the following sequence:

Ala-Gln-Thr-Ala-Arg-Gln-His-Pro-Lys-Met-His-Leu.

or a portion thereof and n is 0 or 1.

The LT mutein can be recovered in a higher yield and purified more efficiently under mild conditions which does not harm the LT's biological activity, than the whole LT.

8 Claims, 4 Drawing Sheets

5,175,268

DNA ENCODING RECOMBINANT HUMAN LYMPHOTOXIN

This is a divisional of copending application Ser. No. 07/136,029 filed on Dec. 21, 1987, now abandoned.

FIELD OF THE INVENTION

This invention relates to a polydeoxyribonucleic acid (hereinafter referred to as DNA) having genetic information of a novel bioactive polypeptide.

This invention also relates to a replicable recombinant DNA containing the above DNA and a microorganism or a cell transformed with the replicable recombinant DNA, and further relates to the novel bioactive polypeptide obtained by expression of the DNA's genetic informations and a process for producing the same.

In this specification, amino acids and peptides are indicated by the abbreviations adopted by IUPAC-IUB Committee of Biochemistry Nomenclature (CBN). For example, the following abbreviations are used. When the optical isomer is capable of existing with respect to the amino acids and the like, the L-form is represented unless otherwise specified.

Gln: Glutamine residue
Asp: Aspartic acid residue
Pro: Proline residue
Tyr: Tyrosine residue
Val: Valine residue
Lys: Lysine residue
Glu: Glutamic acid residue
Ala: Alanine residue
Asn: Asparagine residue
Leu: Leucine residue
Phe: Phenylalanine residue
Gly: Glycine residue
His: Histidine residue
Ser: Serine residue
Thr: Threonine residue
Ile: Isoleucine residue
Trp: Tryptophan residue
Arg: Arginine residue
Met: Methionine residue Also in this specification, polymers or oligomers of DNA are indicated by the sequence of the following abbreviations:

A: 2'-Deoxyadenylic acid residue
C: 2'-Deoxycytidylic acid residue
G: 2'-Deoxyguanylic acid residue
T: Thymidylic acid residue Unless otherwise stated, the direction from the left to the right in sequence indicates the direction from the 5'-position to the 3'-position.

DESCRIPTION OF THE PRIOR ART

Lymphotoxin (hereinafter referred to as LT) is a protein with an antitumor activity derived from lymphocytes, and is expected to have clinical application in a manner similar to tumor necrosis factor (hereinafter referred to as TNF) derived from macrophages. These LT and TNF have been obtained by adding an endotoxin or a phorbol ester to lymphocytes or macrophages, respectively, for activation thereof. However, with the progress of gene manipulation techniques, the structures of these proteins have recently become identified. As a result, it has become possible to produce these proteins by culturing of a microorganism or a cell using the genes coding for these proteins Gray et al. [Nature, 312, 721(1984)] and Pennica et al. [Nature, 312, 724(1984)] each succeeded in cloning them using the gene manipulation techniques.

On the other hand, even with such a technical progress, a serious problem arises as to extraction of proteins from transformants. With respect to LT described above, there is not known any satisfactory process for extracting LT efficiently from the cells without decreasing its antitumor activity. That is to say, disruption of the cells is required for extracting LT produced in the transformants. If 7M guanidine hydrochloride, 8M urea or 2% sodium dodecyl sulfate (SDS) is used as a denaturant, the activity of LT is seriously influenced to cause irreversible inactivation. Therefore, it has been considered to utilize lysozyme lysis or ultrasonic treatment as a process in which cell disruption conditions are mild. However, these conditions result in a low yield of the product.

SUMMARY OF THE INVENTION

In order to extract the proteins having high antitumor activity in a high yield, the present inventors have constructed various LT genes, using the gene manipulation technique referred to under the technical background described above, had the transformants containing the recombinant DNA express the genetic information and determined the cytotoxicity of the produced LT against cells thus produced. As a result, the present inventors found that LT mutein (genetically-altered LT) wherein 10 to 21 amino acids of LT have been deleted from the N-terminus and which has Pro or Phe at the N-terminus, could be extracted and purified in higher yield under mild conditions without a decrease in its biological activity as compared to the complete LT having all 171 amino acid residues. Based on this information, the present inventors have further studied and thus completed the present invention.

That is to say, the present invention relates to a protein comprising the following amino acid sequence or a portion of an active portion of said protein:

H—(Met)n—R$_1$—R$_2$—Ala—His—Ser—Thr—Leu—Lys—Pro—Ala—
　　Ala—His—Leu—Ile—Gly—Asp—Pro—Ser—Lys—
　　Gln—Asn—Ser—Leu—Leu—Trp—Arg—Ala—Asn—
　　Thr—Asp—Arg—Ala—Phe—Leu—Gln—Asp—Gly—
　　Phe—Ser—Leu—Ser—Asn—Asn—Ser—Leu—Leu—
　　Val—Pro—Thr—Ser—Gly—Ile—Tyr—Phe—Val—
　　Tyr—Ser—Gln—Val—Val—Phe—Ser—Gly—Lys—
　　Ala—Tyr—Ser—Pro—Lys—Ala—Thr—Ser—Ser—
　　Pro—Leu—Tyr—Leu—Ala—His—Glu—Val—Gln—
　　Leu—Phe—Ser—Ser—Gln—Tyr—Pro—Phe—His—
　　Val—Pro—Leu—Leu—Ser—Ser—Gln—Lys—Met—
　　Val—Tyr—Pro—Gly—Leu—Gln—Glu—Pro—Trp—
　　Leu—His—Ser—Met—Tyr—His—Gly—Ala—Ala—
　　Phe—Gln—Leu—Thr—Gln—Gly—Asp—Gln—Leu—
　　Ser—Thr—His—Thr—Asp—Gly—Ile—Pro—His—
　　Leu—Val—Leu—Ser—Pro—Ser—Thr—Val—Phe—
　　Phe—Gly—Ala—Phe—Ala—Leu—OH wherein R$_1$ is Pro or Phe, R$_2$ is a peptide chain represented by the following sequence:

Ala-Gln-Thr-Ala-Arg-Gln-His-Pro-Lys-Met-His-Leu.

or a portion thereof and n is 0 or 1.

Further, the present invention includes a polydeoxyribonucleic acid containing the nucleotide sequence coding for the polypeptide described above and a polydeoxyribonucleic acid containing the sequence complementary thereto.

The present invention relates to a replicable recombinant DNA which can express the polypeptide containing the amino acid sequence described above in a transformed microorganism or cell. As such a recombinant DNA, there can be cited for example pTB620, pTB622, pTB697, pTB 848 and pTB 849.

Furthermore, the present invention relates to a microorganism or a cell transformed by the replicable recombinant DNA capable of expressing the polypeptide shown by the amino acid sequence of LT described above. As such a microorganism or cell, there can be mentioned *Escherichia coli, Bacillus subtilis*, yeast and higher animal cells.

Still furthermore, the present invention relates to a process for producing LT, which comprises expressing the gene coding for LT which has some amino acids deleted from the N-terminus, in a microorganism or cell. More particularly, it relates to a process for producing the polypeptide, which comprises cultivating the transformed microorganism or cell with the replicable recombinant DNA and recovering the peptide efficiently.

Figure 2:
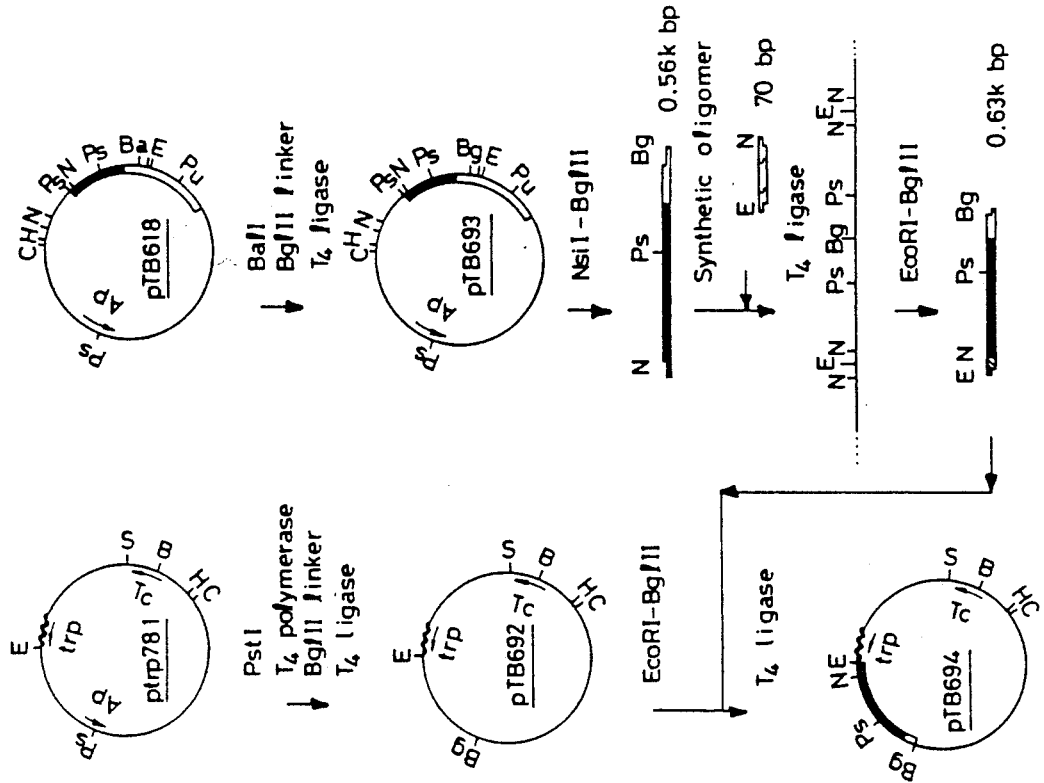
FIGS. 1 to 7 are schematic representations which show the construction of recombinant plasmids pTB622, pTB694, pTB697, pTB848, pTB620, pTB696 and pTB849 respectively.

The abbreviations and their meanings in each figure are as follows:
B: Bal I
Ba: BamH I
Bg: Bgl II
C: Cla I
E: EcoR I
H: Hind III
N: Nsi I
P or Ps: Pst I
Pu: Pvu II
S: Sal I
X: Xho I

DESCRIPTION OF THE PREFERRED EMBODIMENTS

The DNA coding for N-terminal deleted LT of the present invention can be prepared by the following process:

1. m-RNA can be collected by a known method from human peripheral blood lymphocytes in which the synthesis of LT is induced by 12-O-tetradecanoylphorbol-13-acetate (TPA) and concanavalin A (ConA). Further, about $5 \times 10^5$ cDNA library can be prepared therefrom.

2. An oligonucleotide from 10-mer to 50-mer coding for a partial peptide chain of LT is synthesized. By using this oligonucleotide as a probe, the screening of LT cDNA is conducted. For example, when a synthetic nucleotide of 18-mer (TCCAAAGAAGACAGTACT) at the C-terminal side is used, about 50 clones can be obtained.

3. Plasmids are isolated from the LT cDNA clones thus obtained and the nucleotide sequence is determined. A plasmid coding for the amino acid sequence of LT described above is selected, cleaved with an appropriate restriction enzyme, and then suitably inserted into an expression vector. Thus, recombinant DNA containing the DNA fragment can be prepared.

4. Various kinds of hosts, for example *Escherichia coli*, are transformed by using the vector prepared in item 3. Consequently, strains containing DNA coding for LT can be obtained.

5. After the transformant is cultured and the plasmid is isolated in item 4., the DNA coding for N-terminal deleted LT is prepared as follows:

(1) In case of the human LT gene, the restriction enzyme NsiI recognition site is located in the region coding for methionine-histidine situated in the 20th-21st positions from the N-terminus. Then, by digesting the LT gene with NsiI at that site, the DNA fragment coding for N-terminal deleted LT can be obtained. The DNA coding for LT (20-171) is produced by linking an appropriate adapter containing the following sequence with the above fragment and the produced DNA fragment is inserted into an appropriate vector:

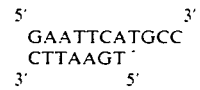

(2) A chemically synthesized DNA fragment is linked with the DNA fragment coding for N-terminal deleted LT which has been cleaved with NsiI. On this occasion, there can be used a DNA fragment coding for a peptide chain corresponding to the chain from alanine situated in the 10th position to methionine situated in the 20th position from the N-terminus, a DNA fragment coding for a peptide chain in which an amino acid or peptide of a portion of the above peptide chain is deleted or substituted with another amino acid or peptide. These may be synthesized so as to maintain the reading frame correctly.

(3) Similarly, in case of the human LT gene, the restriction enzyme Pvu II recognition site is located in the region coding for serine-alanine situated in the 9th-10th positions from the N-terminus. Then, by digesting the LT gene with PvuII at that site, the DNA fragment coding for N-terminal deleted LT can be obtained. A DNA fragment coding for LT (10-171) is produced by linking an appropriate adapter containing the following sequence with the above fragment and the produced DNA fragment is inserted into an appropriate vector:

(4) After the cleavage with PvuII, the DNA fragment coding for N-terminal deleted LT is further treated with an exonuclease such as nuclease BAL31 to remove the region coding for 1-10 amino acids therefrom. Then, by selecting the DNA fragment in which the reading frame of the gene is correctly maintained, the DNA fragments coding for LT (x-171), x=10-20, can be prepared.

(5) The technique of a site-directed mutagenesis (Smith, M. and Gillam, S., Genetic Engineering, 3, 1 (1981)) may also be applied Namely, after the cleavage with PvuII, the DNA fragment coding for N-terminal deleted LT is inserted into vector M13, with which *Escherichia coli* JM103 (Pharmacia P-L Biochemicals) is infected. After cultivation, M13 phages released in the broth are precipitated with polyethylene glycol and treated with phenol, whereby single stranded M13 phage DNA can be obtained.

Then, the DNA coding for a peptide chain in which an amino acid or peptide of a part of the peptide chain from alanine situated in the 10th position to methionine situated in the 20th position from the N-terminus of LT is lacked or substituted with another amino acid or peptide is prepared by a chemical synthesis method and used as a primer. This primer is mixed with the M13 phage DNA fragment previously prepared to form double stranded DNA by DNA polymerase I large fragment. Thereafter, the cyclization thereof can be achieved by T4 DNA ligase. This circular DN is inserted into *Escherichia coli* JM103 and the released M13 phage DNAs are transferred to a filter. Then, by using the synthesized primer which is labeled with $^{32}P$, plaque hybridization [Maniatis, T. et al., Molecular cloning, A Laboratory Manual, Cold Spring Harbor Laboratory, p. 312 (1982)] is carried out. A DNA is prepared from the phage from which a strong signal is detected and cut out with an appropriate restriction enzyme The DNA fragment thus obtained is introduced in a plasmid to provide a DNA fragment coding for modified N-terminal deleted LT.

Plasmid DNA, cosmid DNA, phage DNA and the like containing the whole or a portion of the human LT gene can be used as a template DNA for the site-directed mutagenesis. M13 phage or $\phi$X174 phage is desirable as a template DNA, because a single stranded DNA can be easily prepared therefrom. For example, when M13 phage or $\phi$X174 phage in which the whole or a portion of the human LT gene is introduced is used, the phage particles which are present in the broth are precipitated with polyethylene glycol, deproteinized by phenol treatment, and then precipitated with ethanol, to obtain a single stranded DNA in the phage particle. When a double stranded plasmid DNA or cosmid DNA in which the whole or a portion of the human LT gene is introduced is used as a template DNA, a double stranded DNA is subjected to heat treatment at 100° C. for 1 to 10 minutes, preferably 3 to 5 minutes, and then cooled rapidly with ice water to be denatured to a single stranded DNA, prior to the use.

The primer for the site-directed mutagenesis, may have any DNA sequence so long as it has a DNA sequence to which the sequence shall be changed and functions as the primer on the DNA synthesis through hybridization with a template DNA. Also, the primer may be produced by any method, but it is desirable to prepare a single stranded DNA having an appropriate sequence by a chemical synthesis method. Such a primer is mixed with the single stranded DNA previously prepared, and repaired to a double stranded DNA by DNA polymerase I large fragment. Thereafter, the cyclization can be achieved by T4 DNA ligase. After this circular DNA is introduced into *Escherichia coli*, plaque hybridization (Maniatis, T. et al., Molecular Cloning, A Laboratory Manual, Cold Spring Harbor Laboratory, p. 312 (1982)) or colony hybridization (ibid. p. 326) is carried out, using the primer labeled with a radioisotope as a probe, whereby the desired mutant can be selected. By using phage DNA or plasmid DNA prepared from the plaque or the colony thus obtained, N-terminal deleted LT gene can be prepared.

The recombinant DNA capable of expressing DNA coding for N-terminal deleted LT can be constructed, by inserting the DNA fragment coding for N-terminal deleted LT thus obtained at the 3'-terminus of the promoter region which functions in various hosts such as *Escherichia coli*, *Bacillus subtilis*, yeast and animal cells.

Any promoter region is available, if the region contains a site necessary for initiating the mRNA synthesis by the linkage of RNA polymerase.

For example, when *Escherichia coli* is used as a host, the recombinant DNA capable of expressing DNA coding for N-terminal deleted LT can be constructed by inserting the DNA fragment coding for N-terminal deleted LT at the 3'-terminus of the promoter region capable of functioning in *Escherichia coli*. When the host is *Escherichia coli*, there is used pBR322, pBR325, ptrp781, pUC8, pUC9, pJB8 or the like as the vector, and the DNA fragment coding for N-terminal deleted LT is inserted therein by T4 DNA ligase. By using this reaction solution, *Escherichia coli* such as C600 strain, MM294 strain, DH1 strain, W3110 strain, PR1 strain, PR13 strain, or the like is transformed according to the known method [Cohen, S. N. et al., Proc. Natl. Acad. Sci. USA, 69, 2110 (1972)] or a similar method thereto.

The promoter used is not necessary to be limited to the trp promoter (trp-p). For example, there may be used a recA promoter (Japanese Patent Unexamined Publication No. 59-65099), a lac promoter, a $\lambda P_L$ promoter or the like.

The transformant carrying the novel recombinant plasmid DNA containing the DNA fragment coding for N-terminal deleted LT obtained as described above can be selected as a phenotype, for example, ampicillin resistance type, tetracycline resistance type or resistance type to these both drugs.

The transformant described above is cultured in the known medium. As the medium, there can be mentioned, for example, L-broth, Penassay broth and M-9 medium containing glucose and Casamino Acids (Miller, J., Experiments in Molecular Genetics, 431–433, Cold Spring Harbor Laboratory, New York, 1972). In order to allow the promoter to act efficiently, the drug such as 3$\beta$-indolylacrylic acid may be added thereto if necessary.

The cultivation of the transformant is generally carried out at 15° to 43° C., preferably 28° to 40° C. for 2 to 24 hours, preferably 4 to 16 hours, with aeration or agitation if necessary.

For example, when an animal cell is used as the host, the DNA fragment coding for N-terminal deleted LT is inserted at the 3'-terminus of the region of the promoter capable of functioning in the animal cell, for example an SV40 promoter, and the host is transformed with the recombinant DNA by a known method, and then the transformant is cultured, whereby N-terminal deleted LT can be produced.

When *Bacillus subtilis* or yeast is used as the host, the DNA fragment coding for N-terminal deleted LT is inserted at the 3'-terminus of the region of the promoter capable of functioning in *Bacillus subtilis* or yeast, and the host is transformed with the recombinant DNA by a known method, and then the transformant is cultured, whereby N-terminal deleted LT can be produced.

Regarding vectors, any one can be used selected from a lot of known vectors if it is available for the gene expression. For example, in the case of yeast, there are mentioned pPH017, pGLD906, pGLD906-1, pCDX [Okayama, H., & Berg, P: Mol. Cell. Biol., 3 280(1983)] and pKSV-10 (Pharmacia), and in the case of *Bacillus subtilis*, there are mentioned pUB110, pTB5 and pC195. Regarding promoters, in the case of yeast, for example, there are mentioned PHO5, GLD, PGK, ADH and PHO81 promoter, and in the case of *Bacillus subtilis*, there are mentioned SPO1, SPO2 and pen P.

Of the hosts described above, *Escherichia coli* is more preferable.

After the cultivation; the cells are collected by a known method. In case of the transformant of *Escherichia coli*, the cells are suspended in an appropriate buffer solution, for example Tris-hydrochloric acid buffer (pH 7.5) and disrupted by the ultrasonic treatment, lysozyme and/or freeze-thawing. Thereafter, the supernatant containing N-terminal deleted LT is obtained by centrifugation. Preferably, there can be employed a method wherein the collected cells are suspended in a buffer solution, to which lysozyme is added, and incubated at 0° to 10° C. for 10 minutes to 3 hours, and then treated with ultrasonication at 0 to 10° C. for 30 seconds to 5 minutes, and then centrifuged to obtain the supernatant.

The separation and purification of N-terminal deleted LT from the extract can be carried out by, for example, gel filtration, hydroxyapatite column chromatography, ion-exchange column chromatography, ultracentrifugation and affinity chromatography using human LT antibody.

There are hereinbefore described the methods for obtaining the gene of N-terminal deleted LT and for producing N-terminal deleted LT by using the gene. However, the present invention is not limited thereto.

In the present invention, the whole or a portion of the nucleotide sequence can be substituted with an artificial DNA fragment synthesized chemically, without changing amino acid sequence, due to differences in usage frequency of codon (genetic code) corresponding to each amino acid.

The bioactive polypeptide of the present invention does not exhibit its cytotoxicity to normal cells, but selectively kills tumor cells or transformed cells. Therefore, its usefulness for an anticancer drug is expected. This peptide has biological activity equivalent to that of known LT(1-171) having whole 171 amino acid residues. Moreover, this peptide is produced by the gene manipulation technique and the protein stored in the cell can be recovered in high yield of several ten times compared with that of LT(1-171) described above.

The present invention will hereinafter be described in detail with the following Reference Examples and Examples. It is understood of course that these examples are not intended to limit the scope of the invention.

In carrying out the present invention, preparation of recombinant DNA and insertion of the recombinant into the microorganism were conducted according to the following experimental textbooks unless otherwise stated:

(1) T. Maniatis, E. F. Fritsch, J. Sambrook, Molecular Cloning, published by Cold Spring Harbor Laboratory (U.S.A.), (2) Edited by Y. Takagi, Gene Manipulation Experimental Method, published by Kodansha (JAPAN).

REFERENCE EXAMPLE 1

Evaluation of Cytotoxic Activity against L929 Cell

The cytotoxicity of LT was measured by the method corresponding to that described in J. Immunol. 126, 235 (1981) or J. Immunol. Methods, 70, 257 (1984), using L929 cells. Namely, 50 $\mu$l of L929 cells suspended in a concentration of $4 \times 10^5$ cells/ml in RPMI 1640 medium supplemented with 10% fetal calf serum (FCS) containing 4 $\mu$g/ml of mitomycin C were added to 50 $\mu$l of a sample stepwise twice diluted with RPMI 1640 medium supplemented with 10% fetal calf serum (FCS) by using a microplate for tissue culture (Flow Laboratory Inc.) having 96 wells, and then cultured in 5% carbonic acid gas at 37° C. for 48 hours. After completion of the cultivation, the live cells were dyed with dimethylthiazolyl diphenyltetrazolium bromide (MTT), and dissolved with 10% SDS-0.01N HCl. Thereafter, the optical density at 590 nm was measured with Titertek Multiscan (Flow Laboratory). The optical density obtained is proportional to the number of live cells. The amount of biological activity required for killing 50% of L929 cells was defined as 1 unit/ml, and the biological activity of the sample was represented by unit/ml.

REFERENCE EXAMPLE 2

Collection of Natural LT

In accordance with the method described in Hinuma et al., Microbiol, Immunol., 28, 935 (1984), normal human peripheral blood lymphocytes activated by TPA and ConA were cultivated in RPMI 1640 medium containing 10% fetal calf serum (FCS) in 5% carbonic acid gas at 37° C. for 2 to 3 days, and a solution containing LT was obtained from the culture supernatant.

REFERENCE EXAMPLE 3

Preparation of *Escherichia coli* Strain for Transformation (1)

A colony of *Escherichia coli* DH1 strain was cultivated in SOB medium [the experimental textbook (1), p. 69], until an optical density at 550 nm was reached to 0.5. Then, 30 ml of the culture was collected and suspended in 12 ml of 0.2M acetate buffer solution (pH 5.8) containing 0.1 M RbCl, 10 mM $CaCl_2$, 50 mM $MnCl_2$ and 15% glycerol. After cooled with ice for 5 minutes, the suspension was centrifuged. Then, the resulting mixture was resuspended in mM MOPS buffer (pH 6.5) containing 10 mM RbCl, 75 mM $CaCl_2$ and 15% glycerol. The resulting suspension was cooled with ice for 15 minutes then rapidly frozen with dry ice-ethanol, and thereafter stored at $-70°$ C.

REFERENCE EXAMPLE 4

Preparation of *Escherichia coli* strains for Transformation (2)

Colonies of *Escherichia coli* strains DH1, C600 and MM294 were cultivated in 10 ml of SOB medium, until an optical density at 550 nm reached to 0.3. After cooled with ice, the resulting culture was centrifuged. The cells obtained were washed with 5 ml of 10 mM NaCl. The cells were resuspended in 5 ml of 50 mM $CaCl_2$ and allowed to stand for 15 minutes under ice cooling. After centrifugation, the cells were suspended in 0.5 ml of 50 mM CaCl$_2$ and used immediately thereafter.

REFERENCE EXAMPLE 5

Preparation of Yeast strain for transformation

According to the method of Beggs, J. D. et al., colonies of *Saccharomyces cerevisiae* AH22R$^-$ were cultured overnight in the YPDA medium (containing 10 g/l yeast extract, 20 g/l polypepton, 10 g/l glucose and 0.4 g/l adenine) without shaking. Then, 4 ml of the culture was collected and the cells were washed with 4 ml of 0.1M sodium citrate (pH 5.8) −0.01M EDTA −1.2M sorbitol. Thereafter the cells were suspended in 4 ml of 1 mg/ml Zymolyase 100T (Seikagaku Kogyo, Japan) −0.1M sodium citrate (pH 5.8) −0.01M EDTA −1.2M sorbitol, and the suspension was reacted for 2 hours at 30° C. to lyse the cell wall. The cells were washed twice with 10 mM CaC$_2$ −1.2M sorbitol and suspended in 0.1 ml of the same solution. The suspension was used immediately for transformation.

EXAMPLE 1

Preparation of cDNA Library by Using mRNA Derived from Human Lymphocytes

The lymphocytes prepared from human peripheral blood were cultivated in RPMI 1640 medium (supplemented with 10% FCS) containing TPA (15 ng/ml) and ConA (40 μg/ml) at 37° C. to induce LT. After 24 hours, $1 \times 10^{10}$ cells of the induced human lymphocytes were disrupted for denaturation by a Teflon homogenizer in a solution containing 5M guanidine thiocyanate, 5% mercaptoethanol, 50 mM Tris-HCl (pH 7.6) and 10 mM EDTA. Thereafter, sodium N-lauroyl sarcosinate was added thereto to a concentration of 4%, and the homogenized mixture was layered on 6 ml of 5.7M cesium chloride solution (5.7M cesium chloride and 0.1M EDTA). The resulting mixture was centrifuged by a Beckmann SW28 rotor at 24,000 r.p.m. at 15° C. for 48 hours, whereby the precipitate of RNA was obtained. After this precipitate of RNA was dissolved in 0.25% sodium N-lauroyl sarcosinate solution, precipitation with ethanol was carried out, whereby 10 mg of RNA was obtained. The RNA fragment thus obtained was adsorbed on an oligo (dT) cellulose column in a high salt solution (0.5M NaCl, 10 mM Tris-HCl (pH 7.6), 1 mM EDTA and 0.3% SDS), and 300 μg of mRNA containing poly (A) was obtained by elution of mRNA containing poly (A) with a low salt solution [10 mM Tris-HCl (pH 7.6), 1 mM EDTA and 0.3% SDS].

The mRNA thus obtained was further precipitated with ethanol, and dissolved in 0.2 ml of a solution [10 mM Tris-HCl (pH 7.6), 2 mM EDTA and 0.3% SDS]. After treatment at 65° C. for 2 minutes, fractionation by 10-35% sucrose density gradient centrifugation (by a Beckmann SW28 rotor, at 25,000 r.p.m. at 20° C. for 21 hours) was conducted. For each of the fractions, a part of RNA was injected into oocyte cells of *Xenopus leavis* and the LT activity in protein to be synthesized was measured. As a result, the activity of LT was detected in the fraction corresponding to a sedimentation constant of about 16S. The amount of LT mRNA in this fraction was about 25 μg.

Using the poly(A) RNA as a template, a cDNA library was prepared by using pcDV1 vector and pL1 linker according to the method of Okayama and Berg [Mol. Cell. Biol., 2, 161 (1982); ibid. 3, 280 (1983)]. *Escherichia coli* DH1 was infected with circular vector plasmids containing cDNA, and a cDNA library of about $5 \times 10^5$ clones of which the host was *Escherichia coli* DH1 could be obtained from 5 μg of poly(A) RNA.

EXAMPLE 2

Isolation of Plasmid Containing Human LT cDNA and Determination of Nucleotide Sequence Thereof The above human cDNA library using *E. coli* DH1 was: inoculated to 10 nitrocellulose filters (Millipore, HATF filter) up to $3 \times 10^4$ clone/filter Twenty (20) replica filters (each pair consisting of 2 filters) were prepared from the above 10 master filters. Plasmid DNA exposed for denaturation by lysing *Escherichia coli* on the replica filter with 0.5N NaOH solution was dried for fixation on the filter [Grunstein, M., Hogness, D. S., Proc. Natl. Acad. Sci. USA, 72, 3961 (1975)].

On the other hand, an oligonucleotide having the following formula, which corresponded to a portion (the gene portion corresponding to amino acid No. 162-167) of the nucleotide sequence of the LT gene already reported (Gray et al., Nature, 312, 721 (1984)), was synthesized and used as a screening probe for human LT cDNA:

$$5' \qquad\qquad\qquad 3'$$
$$\text{TCCAAAGAAGACAGTACT}$$

The 5'-terminus of the oligonucleotide probe was labeled with $^{32}$P by using T4 polynucleotide kinase and $[\gamma-^{32}\text{P}]$-ATP.

The labeled probe was hybridized with each of the replica filters on which DNA was fixed. The hybridization reaction was carried out at 40° C. for 16 hours in 10 ml of a solution of $5 \times$SSC (0.15M NaCl, 0.015M sodium citrate), $5 \times$Denhardt's, 0.1% SDS and 100 μg/ml of denatured salmon sperm DNA. After completion of the reaction, the filters were washed with a solution of $6 \times$SSC and 0.1% SDS at room temperature for 30 minutes 3 times and further at 43° C. for 60 minutes twice [the experimental textbook (1), p. 309]. Radioautograms were taken from the washed filters and the radioautograms of the replica filters in sets of two filters were put together in layers for searching the cells reactive to the probe. By this method, 50 strains of *E. coli* DH1 strain reactive to the probe were obtained from about $3 \times 10^5$ colonies.

The plasmid DNA was extracted and purified from these cells by the alkaline method (Birnboim, H. C., Doly, J., Nucleic Acids Res., 7, 1513 (1979)). The DNA was cleaved by the restriction enzyme BamHI (Takara Syuzo Inc.) and fractionated by agarose gel electrophoresis. Thereafter, the DNA fragments were transferred on a nitrocellulose filter (BA85 manufactured by S & S Inc.) [Southern blotting method, the experimental textbook (1), p. 382]. When this filter was hybridized with the oligonucleotide probe described above, the plasmid DNA fragments reacted with the probe.

Then, one strain of *E. coli* K12 DH1/pTB618 having the plasmid which had the largest BamHI DNA fragments (cDNA portions) among others was selected. The nucleotide sequence of the cDNA portion of this plasmid DNA was determined by the dideoxynucleotide synthetic chain termination method [J. Messing et al., Nucleic Acids Res., 9, 309 (1981)].

As a result, it was proven that the LT gene contained in plasmid pTB618 was not complete one and contained from the non-translated portion on the 3' terminal side upstream to the third C of codon CCC of Pro which was the 18th amino acid.

EXAMPLE 3

Construction of Human LT (21-171) Expression Vector pTB622

The plasmid pTB618 prepared above was cleaved by restriction enzymes NsiI (Takara Syuzo INC.) and BamHI, and a DNA fragment of 1.1 kilo base pair (hereinafter referred to as Kbp) containing the LT gene was separated. T4 DNA polymerase (PL Inc.) was reacted with the DNA fragment to change the termini of the product to flush ends. Thereafter, an EcoR I linker accompanied with ATG of 16-mer (AACATGAATT-CATGTT) was ligated therewith by T4 DNA ligase for adjusting the frame. After T4 DNA ligase was inactivated by heat treatment at 65° C. for 10 minutes, digestion was carried out with restriction enzyme EcoRI, and a DNA fragment of 0.6 Kbp containing the LT gene linked with the linker was separated by agarose electrophoresis.

Figure 1:
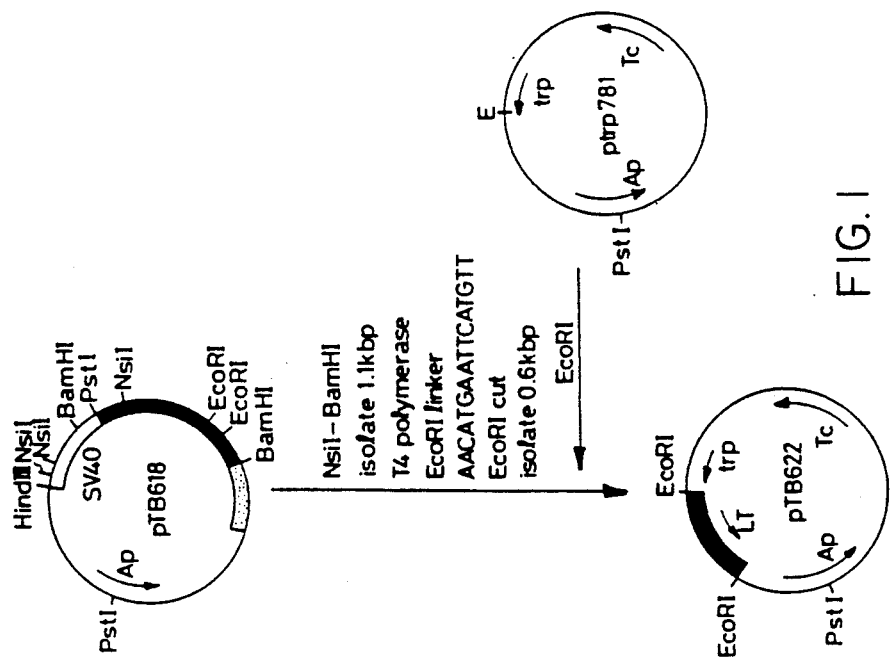

On the other hand, the plasmid ptrp781 described in Kurokawa, T. et al., Nucl. Acids Res. 11, 3077(1983) was cleaved by restriction enzyme EcoRI, and phosphate of the 5'-terminus was removed by alkaline phosphatase treatment. The thus obtained DNA fragment was mixed with the LT DNA fragment of 0.6 Kbp linked with the EcoRI linker accompanied with ATG, and T4 DNA ligase was allowed to act on the mixture, whereby human LT expression vector pTB622 for Escherichia coli was constructed in which the LT gene was inserted downstream of the tryptophan promoter (FIG. 1).

EXAMPLE 4

Construction of Human LT (1-171) Expression Vector pTB694

PROCESS 1

Preparation of pTB693 Plasmid DNA

As shown in FIG. 2, 2 μg of plasmid pTB618 was digested at 37° C. for 6 hours by using 0.6 unit of BalI (Takara Syuzo Inc.).

On the other hand, 2 μg of a BglII linker of 8-mer represented by CAGATCTG was phosphorylated with 0.5 mM ATP and 2.5 units of T4 polynucleotide kinase. Then, 0.2 μg of the phosphorylated linker was added to 1.6 μg of BalI-digested pTB618, and the mixture was reacted in the presence of T4 DNA ligase at 14° C. overnight. After inactivation at 65° C. for 5 minutes, the reaction product was trimmed by 30 units of BglII, and subjected to 1.2% agarose gel electrophoresis.

A main band corresponding to 4.3 Kbp was cut out, extracted with Tris-hydrochloric acid buffer, and then purified by an RDP minicolumn (Bio RAD). To 100 ng of the linear DNA fragment described above, 10 units of T4 DNA ligase was added to obtain DNA containing pTB693 plasmid, with which Escherichia coli DH1 strain was transformed according to a conventional method. In detail, the DH1 cells for transformation prepared and stored in the frozen state at −70° C. in Reference Example 3 were slowly thrawed under ice cooling, and 30 ng of the DNA containing pTB693 was added to 100 μl of the suspension thereof. After reaction for 30 minutes under ice cooling, heat shock was given to the reaction product at 42° C. for 90 seconds. The mixture was thereafter cooled with ice for 1 to 2 minutes. SOB medium containing 0.2 ml of 20 mM glucose was added thereto, and cultivation was conducted at 37° C. for 1 hour. The suspension was inoculated on an LB agar plate containing 35 μg/ml of ampicillin, and cultivated at 37° C. overnight. As a result, colonies of ampicillin-resistant transformants could be obtained from plasmid pTB693.

The above described Escherichia coli DH1 strain containing plasmid pTB693 was cultivated in 250 ml of an LB medium containing 35 μg/ml of ampicillin [the experimental textbook (1, p. 68)]. Then, by isolating the plasmid in accordance with the method described in the experimental textbook, p. 88, about 300 μg of pTB693 was obtained.

PROCESS 2

Preparation of Human LT-cDNA

50 μg of pTB693 plasmid was digested by 100 units of NsiI and 120 units of BglII (Takara Syuzo Inc.) at 37° C. for 1 hour, and then subjected to 2% agarose gel electrophoresis. A band of 0.56 Kbp corresponding to the NsiI-BglII fragment containing LT-cDNA was cut out and purified by an RDP minicolumn described in Process 1.

On the other hand, the following 6 oligonucleotide chains coding for N-terminal peptide (1-20) of LT were chemically synthesized using a Model 380A-DMA synthesizer of Applied Biosystems Inc.(USA) (Tetrahedron Lett., 21, 3243 (1980)):

The 5'-terminus of LT gene

```
            1                                            10
            Leu Pro Gly Val Gly Leu Thr Pro Ser Ala—
AATTCT ATG CTC CCT GGT GTT GGC CTC ACA CCT TCA GCT—
    GA TAC GAG GGA CCA CAA CCG GAG TGT GGA AGT CGA—
(EcoR I)                                         (Pvu II)
```

```
                                    20
Ala Gln Thr Ala Arg Gln His Pro Lys Met
GCC CAG ACT GCC CGT CAG CAC CCC AAG ATG CA
CGG GTC TGA CGG GCA GTC GTG GGG TTC T
                                   (Nsi I)
```

Synethetic oligonucleotides

```
  #1                                    #3
AATTCT ATG CTG CCT GGT GTT GGT |CTG ACA   CCT TCA GCT—
    GA TAC GAC GGA CCA CAA CCA  GAC TG|T  GGA AGT CGA—
  #2                                    #4
```

```
         #5
GCT CAG ACT |GCT AGA CAG CAT CCT AAG ATG CA
CGA GTC TGA  CGA T|CT GTC GTA GGA TCC T
                #6
```

To the mixture of each 1 μg of these chains, 12.5 units of T4 polynucleotide kinase and 1 mM ATP were added, and phosphorylation was conducted at 37° C. for 1 hour. After inactivation at 70° C. for 5 minutes, the mixture was further reacted with 350 units of T4 DNA ligase at 14° C. overnight. After inactivation at 65° C. for 5 minutes, 45 units of EcoRI (Takara Syuzo Inc.) and 35 units of NsiI were added to the mixture where the reaction was completed (containing about 3.5 μg of DNA), and digestion was carried out at 37° C. for 2 hours. Then, the mixture was subjected to 10% polyacrylamide gel electrophoresis.

A band corresponding to about 70 bp was cut out and purified by an RDP minicolumn.

To 30 ng of the above described EcoRI-NsiI fragment of about 70 bp, 110 ng of the NsiI-BglII fragment of 0.56 Kbp was added, and the mixture was reacted in the presence of 35 units of T4 DNA ligase at 14° C. for 2 hours. As to the mixture where the reaction was completed, digestion and trimming were carried out by 6 units of BglII and 9 units of EcoRI at 37° C. for 1 hour, whereby cDNA of 0.63 Kbp coding for the whole amino acid sequence of human LT (1-171) could be prepared.

PROCESS 3

Preparation of pTB692 plasmid DNA

2 μg of plasmid ptrp781 was digested with 32 units of PstI (Takara Syuzo Inc.) at 37° C. for 1 hour. After completion of the reaction, TNE buffer solution [the experimental textbook (1), p. 448] and SDS for giving a final concentration of 0.2% were added thereto. Then, extraction with phenol-chloroform and purification were performed.

To 1 μg of PstI digested ptrp781 described above, 0.1 mM XTP and 4 units of T4 DNA polymerase were added. After the mixture was reacted at 37° C. for 5 minutes, TNE buffer and SDS were added thereto. Then, extraction with phenolchloroform and purification were carried out.

Next, 0.2 μg of the phosphorylated BglII linker described in Process 1 and 35 units of T4 DNA ligase were added to 0.8 μg of the ptrp781 DNA described above, and the mixture was reacted at 14° C. overnight. After inactivation at 65° C. for 5 minutes, the reaction product was trimmed by 30 units of BglII, extracted by phenolchloroform, and further purified by a Sepharose 4B column. Thereafter, 10 units of T4 DNA ligase was added to obtain DNA containing pTB692, followed by transformation of *Escherichia coli* DH1 strain with the DNA according to the conventional method described in Process 1. However, an LB agar plate containing 10 μg/ml of tetracycline was used instead of 35 μg/ml of ampicillin. Then, colonies of tetracycline-resistant transformants were obtained. The colony was cultivated in an LB medium comprising 10 μg/ml of tetracycline. The pTB692 plasmid was obtained according to the method of Process 1.

PROCESS 4

Preparation of pTB694 plasmid DNA 54 units of EcoRI and 30 units of BglII were added to 10 μg of the pTB692 plasmid DNA described in Process 3, and the mixture was reacted at 5° C. overnight. The reaction product was thereafter purified by 1% agarose gel electrophoresis, and a DNA band of 3.3 Kbp was cut out. To 36 ng of this DNA of 3.3 Kbp, 15 ng of the DNA fragment of 0.63 Kbp described in Process 2 was added to obtain DNA containing pTB694 by 10 units of T4 DNA ligase, followed by preparing tetracycline-resistant transformants in accordance with the method described in Process 3. Thus, plasmid pTB694 for expression of human LT (1-171) could be obtained.

EXAMPLE 5

Construction of Human LT (11-171) Expression Vector pTB697

Figure 3:
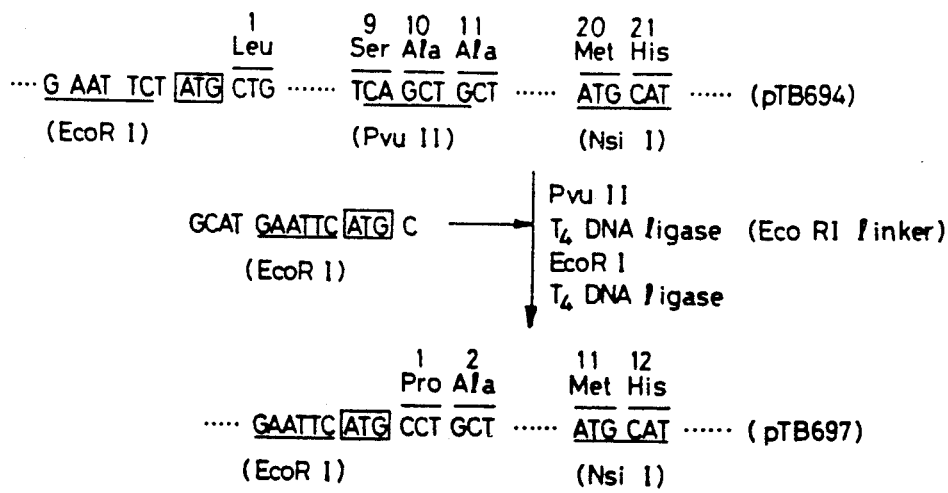

As shown in FIG. 3, 30 units of PvuII (Takara Syuzo Inc.) was added to 10 μg of plasmid pTB694, and the mixture was reacted at 37° C. for 2 hour. Then, extraction with phenol-chloroform and purification were carried out.

On the other hand, 2 μg of the EcoRI linker of 14-mer represented by GCATGAATTCATGC was phosphorylated by 0.5 mM ATP and 2.5 units of T4 polynucleotide kinase. Thereafter, 0.5 μg of the resulting product was added to 2 μg of Pvu II-digested pTB694 described above, and the mixture was reacted in the presence of T4 DNA ligase at 14° C. overnight. After inactivation at 65° C. for 5 minutes, the reaction product was trimmed by 45 units of EcoRI, and subjected to 0.8% agarose gel electrophoresis.

A main band corresponding to 3.9 Kbp was cut out, and then purified by using an RDP minicolumn as described in Example 4, Process 1. To 100 ng of the linear DNA fragment, 10 units of T4 DNA ligase was added to obtain DNA containing pTB697 plasmid, with which *Escherichia coli* DH1 strain was transformed according to the conventional method described in Example 4, Process 3. The pTB697 plasmid could be obtained from the transformant thus obtained.

EXAMPLE 6

Figure 4:
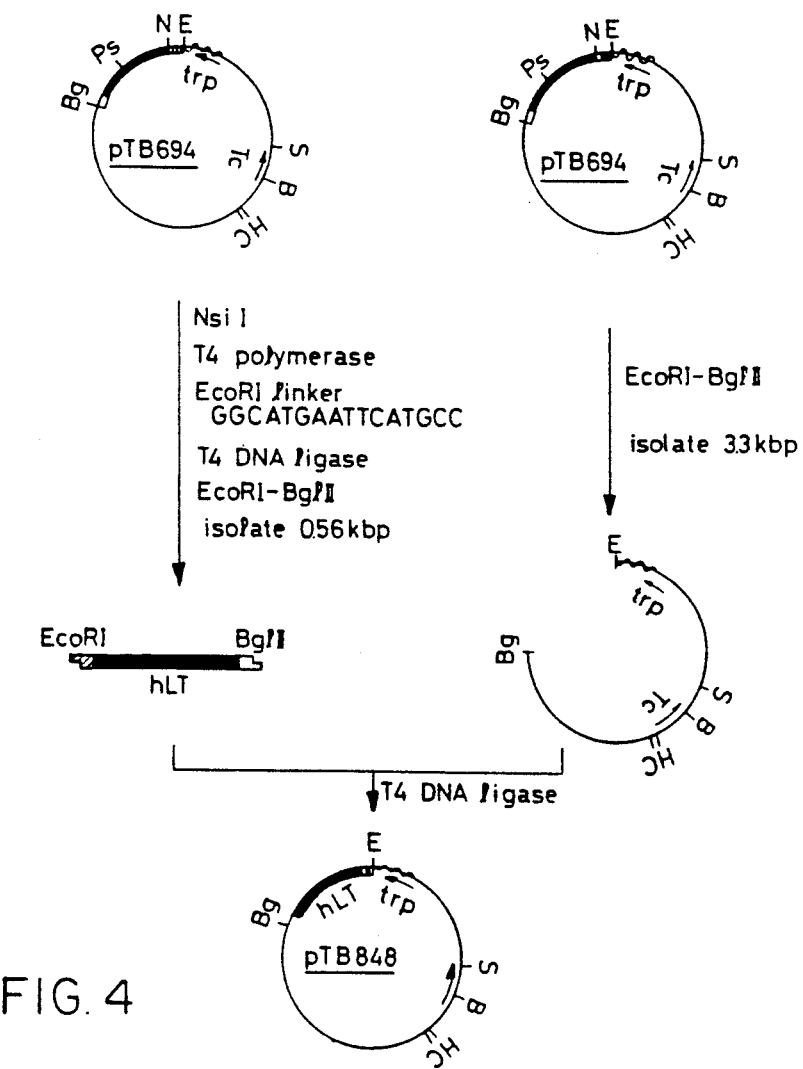

Construction of a vector pTB848 for expression of human LT(21-171) (FIG. 4)

Plasmid pTB694 prepared in Example 4 was cleaved with restriction enzyme NsiI and the ends of the DNA fragment were converted to flush ends with T4 DNA polymerase. An Eco RI linker consisting of 16-mer accompanied with ATG (GGCATGAATTCATGCC) was linked to the above terminus by T4 DNA ligase for adjusting the frame. After T4 DNA ligase was inactivated by heat treatment, the above DNA was cleaved with two restriction enzymes EcoRI and BglII, and a DNA fragment of 0.56 Kbp was separated by agarose electrophoresis.

On the other hand, the same plasmid pTB694 was cleaved with EcoRI and BglII. Thereafter the above described DNA fragment of 0.56 Kbp was added thereto and ligated by T4 DNA ligase to construct human LT expression vector pTB848 where the LT gene was inserted downstream from the tryptophan promoter (FIG. 4).

EXAMPLE 7

Figure 5:
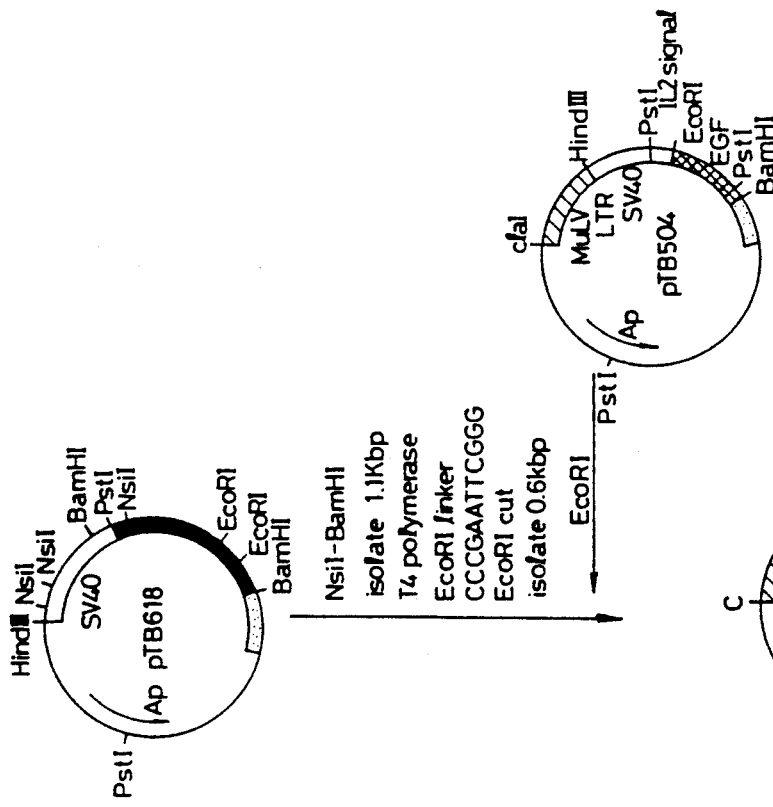

Construction of Human LT (21-171) Animal Cell Expression Vector pTB620 (FIG. 5)

Plasmid pTB618 was cleaved by restriction enzymes NsiI and BamHI, and a DNA fragment of 1.1 Kbp containing the LT gene was separated. T4 DNA polymerase was reacted with the DNA thus obtained to render the ends flush. Thereafter, the EcoRI linker of 12 mer (CCCGAATTCGGG) was ligated therewith by T4 DNA ligase for adjusting the frame. After T4 DNA ligase was inactivated by heat treatment at 65° C. for 10 minutes, digestion was carried out by restriction enzyme EcoRI, and a DNA fragment of 0.6 Kbp containing the LT gene ligated with the linker was separated by agarose electrophoresis.

On the other hand, plasmid pTB504 described in the specification of Japanese Patent Application No. 61-182457 (filed on Aug. 1, 1986) [JP-A-62175182 corresponding to EP-A-0225701] was cleaved by the restriction enzyme EcoRI, and phosphate of the 5'-terminus was removed by alkaline phosphatase treatment. The DNA thus obtained was mixed with the LT DNA fragment of 0.6 Kbp which was ligated with the EcoRI linker accompanied with ATG, and T4 DNA ligase was allowed to act on the mixture, to construct vector pTB620 for expression in animal cells expressing the human LT gene accompanied with the IL-2 leader sequence, under the control of A-MuLV-LTR and the SV 40 promoter (FIG. 5).

EXAMPLE 8

Expression of Gene Coding for Human LT in Animal Cell

Monkey COS-7 cells were cultured in monolayer (Falcon: diameter of 60 mm, plastic dish) in Dulbecco's modified Eagle's MEM (DMEM) medium containing 10% FCS, followed by exchanging the medium for the same medium. After 4 hours from the exchange, calcium phosphate gel containing 10 μg of the DNA of plasmid pTB620, which was prepared according to a known method (Graham et al., Virology, 52, 456 (1973)), was added to the cells, whereby COS-7 cells infected with pTB620 were obtained. After 4 hours, the COS-7 cells infected with pTB620 described above were treated with glycerol, and cultivation was continued to be cultured in the medium containing 0.5% FCS. After 70 to 72 hours, the medium containing produced human LT was collected.

EXAMPLE 9

Construction of Vector pTB696 for Expression of Human LT (1-171) in Animal Cell

Figure 6:
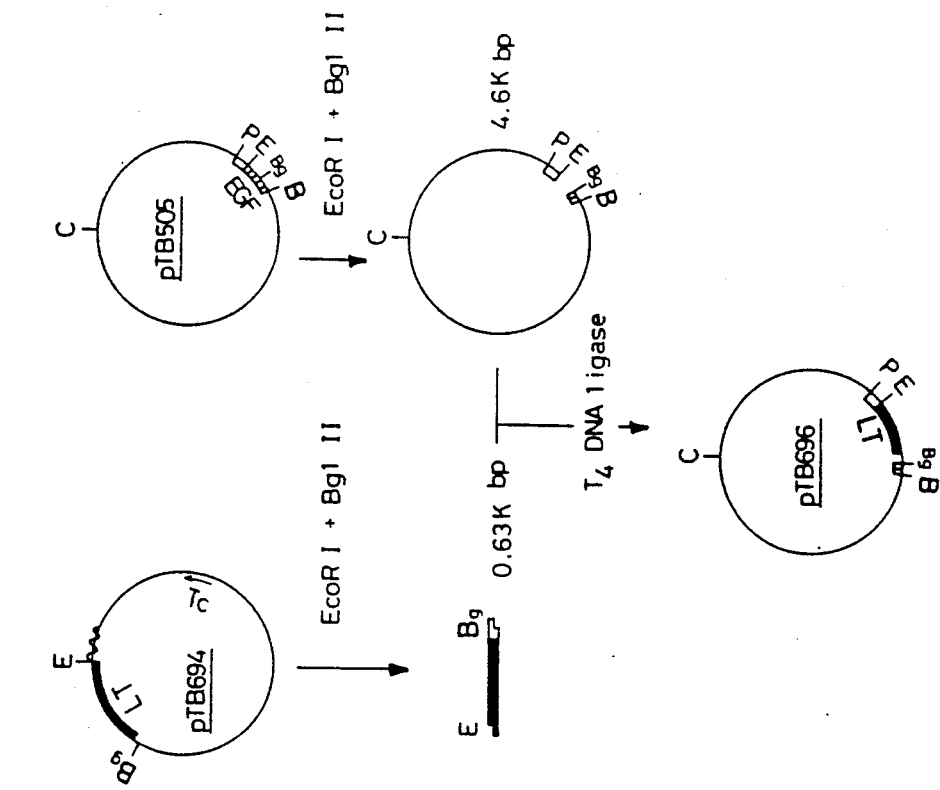

As shown in FIG. 6, 9 units of EcoRI and 12 units of BglII were added to 1 μg of plasmid pTB505 (Japanese Patent Application No. 61-182457) for expression in animal cells, and the mixture was reacted at 37° C. for 2 hours. Thereafter, the reaction product was purified by 1.5% agarose gel electrophoresis, in accordance with a conventional method to prepare 4.6 Kbp DNA.

On the other hand, 45 units of EcoRI and 36 units of BglII were similarly added to 10 μg of pTB694, and the mixture was reacted at 37° C. for 2 hours. Then, 0.63 Kbp DNA containing LT-cDNA was cut out and purified by 1.5% agarose gel electrophoresis.

Two kinds of the DNAs of 4.6 Kbp and 0.63 Kbp described above were mixed with each other in amounts of 14 ng and 50 ng, respectively. The mixture was reacted in the presence of 10 units of T4 DNA ligase at 12° C. for 2 hours to obtain DNA containing pTB696 plasmid, with which *Escherichia coli* DH1 strain was transformed according to the conventional method described in Example 4, Process 1.

The monkey COS-7 cell was transformed with the above described pTB696 plasmid according to the method described in Example 8, to secrete human LT in a culture medium from the transformant.

EXAMPLE 10

Figure 7:
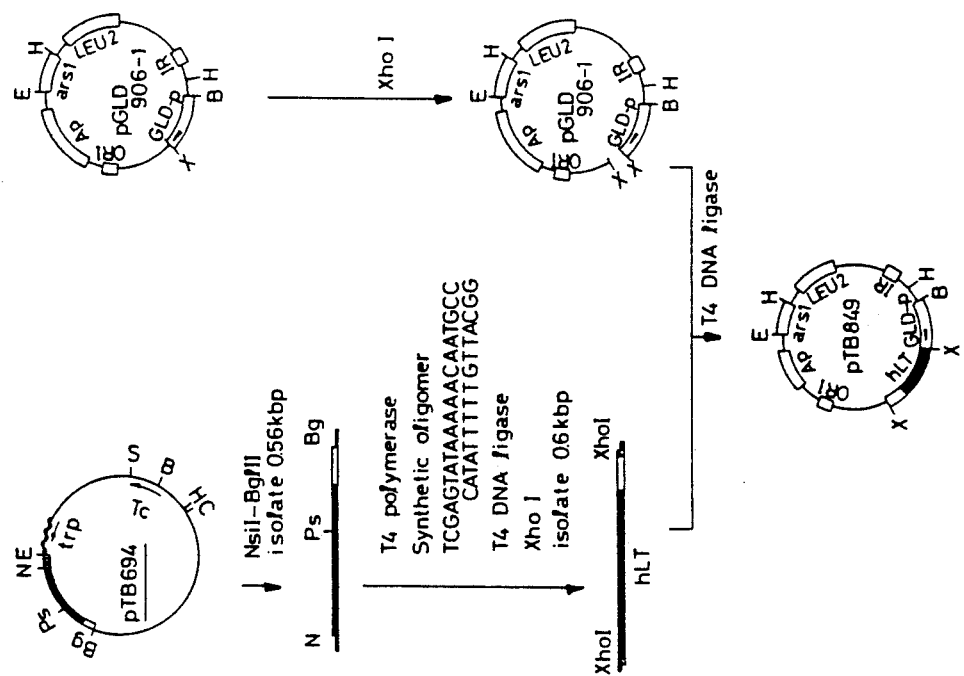

Construction of vector pTB849 for expression of human LT(21-171) in yeast (FIG. 7)

The plasmid pTB694 was cleaved with restriction enzymes NsiI and BglII to obtain a DNA fragment of 0.56 Kbp containing the LT gene. The ends of the DNA fragment were converted to flush end by reaction with T4 DNA polymerase. Thereafter a synthesized DNA oligomer of 20 mer (TCG AGT ATA AAA ACA ATG CC
 CA  TAT TTT TGT TAC GG)

was linked thereto with T4 DNA ligase. After inactivation of T4 DNA ligase by a heat treatment, the above obtained DNA fragment was cleaved with restriction enzyme XhoI, and a DNA fragment of 0.6 Kbp containing the LT gene linked with the XhoI linker was separated by agarose gel electrophoresis.

On the other hand, the plasmid pGLD 906-1 described in Itoh, Y et al., "Biochem. Biophys. Res. Comm." 138, 268 (1986) was cleaved with restriction enzyme XhoI. The obtained DNA was mixed with the above described DNA fragment of 0.6 Kbp, and the mixture was reacted with T4 DNA ligase to construct the expression vector pTB849 in yeast, which had the human LT gene downstream from the GLD promoter (FIG. 7).

EXAMPLE 11

Evaluation of Cytotoxic Activity

1. Expression of Human LT in *Escherichia coli* Strain

DH1 and C600 strains of *Escherichia coli* described in Reference Example 4 were transformed by using plasmids pTB622, 694, 697 and 848 prepared in Examples 3, 4, 5 and 6.

The obtained transformant was cultivated in 4 ml of the M9-CA medium [the experimental textbook (1), p. 69] at 37° C. for 4 hours. After 25 μg/ml of indoleacrylic acid was added thereto, cultivation was further continued for 4 hours. The collected cells were suspended in 0.3 ml of Tris.hydrochloric acid buffer (pH 7.5) containing 0.01% lysozyme and 10% sucrose. The suspension was reacted at 5° C. for 1 hour, and then treated with ultrasonication for 45 seconds, under ice cooling.

The DH1 transformants with pTB622, 694 and 697 were compared in cytotoxic activity in Table 1.

In Table 2, colonies of the C600 transformants with pTB622 and 694 were compared in cytotoxic activity. The pTB622/C600-11 transformant showed the highest biological activity.

In Table 3, the DH1 transformants with pTB694 and 848 were compared in cytotoxic activity.

TABLE 1

Cytotoxic activity of DH1 transformants against L929 cell

| Plasmid | Expressed peptide | Colony No. | Cytotoxic activity Unit/ml | Average | Ratio |
|---|---|---|---|---|---|
| pTB694 | LT(1-171) | 1 | $6.8 \times 10^4$ | $6.1 \times 10^4$ | 1 |
|  |  | 2 | $5.5 \times 10^4$ |  |  |
|  |  | 3 | $5.9 \times 10^4$ |  |  |
| pTB697 | LT(11-171) | 1 | $4.3 \times 10^6$ | $4.5 \times 10^6$ | 74 |
|  |  | 2 | $5.1 \times 10^6$ |  |  |
|  |  | 3 | $4.1 \times 10^6$ |  |  |
| pTB622 | LT(21-171) | 1 | $4.0 \times 10^6$ | $5.2 \times 10^6$ | 85 |
|  |  | 2 | $6.6 \times 10^6$ |  |  |
|  |  | 3 | $4.9 \times 10^6$ |  |  |

TABLE 2

Cytotoxic activity of C600 transformants against L929 cells

| Colony No. | Cytotoxic activity (unit/ml) pTB622 | pTB694 |
|---|---|---|
| 1 | $2.7 \times 10^6$ | $1.8 \times 10^5$ |
| 2 | $2.6 \times 10^6$ | $7.9 \times 10^4$ |
| 3 | $3.2 \times 10^6$ | $1.6 \times 10^5$ |
| 4 | $4.6 \times 10^6$ | $2.2 \times 10^5$ |
| 5 | $2.7 \times 10^6$ | $8.6 \times 10^4$ |
| 6 | $2.6 \times 10^6$ | $8.5 \times 10^4$ |
| 7 | $1.9 \times 10^6$ | $6.8 \times 10^4$ |
| 8 | $2.3 \times 10^6$ | $9.7 \times 10^4$ |
| 9 | $3.7 \times 10^6$ | $2.9 \times 10^5$ |
| 10 | $3.0 \times 10^6$ | $1.6 \times 10^5$ |
| 11 | $5.1 \times 10^6$ | $1.2 \times 10^5$ |
| 12 | $2.7 \times 10^6$ | $2.3 \times 10^5$ |
| 13 | $4.6 \times 10^6$ | $1.9 \times 10^5$ |
| 14 | $2.9 \times 10^6$ | $1.8 \times 10^5$ |
| Average | $(3.18 \pm 0.96) \times 10^6$ | $(1.60 \pm 0.80) \times 10^5$ |

TABLE 3

Cytotoxic activity of DH1 transformants against L929 cell

| Plasmid | Expressed peptide | Colony No. | Cytotoxic activity Unit/ml | Mean | Ratio |
|---|---|---|---|---|---|
| pTB694 | LT(1-171) | 1 | $4.9 \times 10^4$ | $5.2 \times 10^4$ | 1 |
|  |  | 2 | $5.2 \times 10^4$ |  |  |
|  |  | 3 | $5.4 \times 10^4$ |  |  |
| pTB848 | LT(21-171) | 1 | $6.1 \times 10^6$ | $6.8 \times 10^6$ | 131 |
|  |  | 2 | $6.5 \times 10^6$ |  |  |
|  |  | 3 | $7.8 \times 10^6$ |  |  |

2. Secretion of Human LT in Monkey COS-7 Cell

Plasmids pTB620 and 696 for expression in animal cells prepared in Examples 7 and 9 were each transfected to the monkey COS-7 cells. The transformants thus obtained were cultivated by the method described in Example 8. Then, cytotoxic activity against L929 cells of the culture supernatants and the extracts from the cells disrupted with ultrasonication were measured. The results shown in Table 4 were obtained.

TABLE 4

Cytotoxic activity of monkey COS-7 cell transformants against L929 cells

| Plasmid | Expressed peptide | Experimental No. | Cytotoxic activity (unit/ml) Culture supernatant | Cell extracted solution |
|---|---|---|---|---|
| pTB696 | LT(1-171) | 1 | $4.5 \times 10^3$ | $2.4 \times 10^3$ |
|  |  | 2 | $2.1 \times 10^3$ | $1.0 \times 10^3$ |
| pTB620 | LT(21-171) | 1 | $9.0 \times 10^3$ | $3.0 \times 10^3$ |

3. Expression of Human LT in yeast

*Saccharomyces cerevisiae* AH22R⁻ described in Reference Example 5 was transformed by using the plasmid pTB 849 prepared in Example 10.

The obtained transformant was cultivated for a few days at 30° C. in 5 ml of modified Burkholder minimum medium containing 8% sucrose [Toh-E, A et al. J. Bacteriol. 113, 727 (1973)] while being adjusted to pH 6–7 by 25% aqueous ammonia.

After completion of the cultivation, the culture supernatant and cells were separated by centrifugation. The cells were further lysed with Zymolyase followed by centrifugation to collect cell extract. By measuring cytotoxic activity of the supernatant and the extracts against L929 cells, the results shown in Table 5 were obtained.

TABLE 5

Cytotoxic activity of the yeast transformant against L929 cells

| Plasmid | Expressed peptide | colony No. | Cytotoxic Activity (unit/ml) Supernatant | Extract |
|---|---|---|---|---|
| pTB849 | LT(21-171) | 1 | <100 | 840 |
|  |  | 2 | <100 | 870 |
|  |  | 3 | <100 | 970 |
|  |  | 4 | <100 | 1150 |
|  |  | 5 | <100 | 1240 |

EXAMPLE 12

Purification of Human LT

*Escherichia coli* Strains DH1, C600 and MM294 for transformation described in Reference Example 4 were transformed by using plasmid pTB622 prepared according to the method described in Example 3, and colonies showing expression in large amounts were selected. The results were as shown in Table 6.

TABLE 6

Cytotoxic activity of various transformants against L929 cells

| Cell strain | Colony No. | Cytotoxic activity unit/ml | Average | Ratio |
|---|---|---|---|---|
| DH1 | 1 | $3.0 \times 10^6$ | $4.0 \times 10^6$ | 1 |
|  | 2 | $4.0 \times 10^6$ |  |  |
|  | 3 | $4.9 \times 10^6$ |  |  |
| C600 | 1 | $2.7 \times 10^6$ | $1.4 \times 10^7$ | 3.5 |
|  | 2 | $1.2 \times 10^7$ |  |  |
|  | 3 | $2.6 \times 10^7$ |  |  |
| MM294 | 1 | $4.7 \times 10^6$ | $5.2 \times 10^6$ | 1.3 |
|  | 2 | $5.4 \times 10^6$ |  |  |
|  | 3 | $5.6 \times 10^6$ |  |  |

C600-3 which showed the highest biological activity was cultivated in 1.5 l of M9-CA medium at 37° C. After about 4 hours, 25 μg/ml of indoleacrylic acid was added thereto, and cultivation was further continued at 37° C. for 4 hours. After collection of the cells by centrifugation, the cells were disrupted by treatment of 0.03% lysozyme and ultrasonic treatment repeated 4 times, whereby an extract (A) containing human LT was obtained. The specific activity of this extract was $1.1 \times 10$ U/mg.

Then, the extract was added to a DEAE-Sepharose CL-6B column (Pharmacia Inc.) equilibrated with 5 mM phosphate buffer (pH 8.0), and washed with the same buffer, followed by elution with the same buffer containing 0.1M NaCl to provide a roughly purified solution (B) having a specific activity of $7.8 \times 10^5$ U/mg.

After adjusted to pH 6.0 by hydrochloric acid, the roughly purified solution (B) described above was added to a Blue Sepharose CL-6B column equilibrated with 5 mM phosphate buffer (pH 6.0) containing 0.1M NaCl, and washed enough, followed by elution with 5 mM phosphate buffer (pH 8.0) containing 0.5M NaCl. The specific activity of the eluate (C) was $7.4 \times 10^6$ U/mg The eluate (C) was further subjected to gel filtration by a Sephacryl S-200 column equilibrated with 5 mM phosphate buffer (pH 7.3) to provide a purified solution (D) having a specific activity of $1.6 \times 10^7$ U/mg. The results thereof were shown in Table 7.

TABLE 7

| Process | Purification of human LT | | | |
|---|---|---|---|---|
| | Amount of protein (mg) | Amount of activity (unit) | Specific activity (U/mg) | Degree of purification |
| Culture extract (A) | 560 | $6.0 \cdot 10^7$ | $1.1 \cdot 10^5$ | 1 |
| DEAE-Sepharose column eluate (B) | 96.5 | $7.5 \cdot 10^7$ | $7.8 \cdot 10^5$ | 7.1 |
| Blue Sepharose column eluate (C) | 7.74 | $5.7 \cdot 10^7$ | $7.4 \cdot 10^6$ | 67 |
| Sephacryl S-200 column eluate (D) | 1.90 | $3.1 \cdot 10^7$ | $1.6 \cdot 10^7$ | 145 |

EXAMPLE 13

Anti-Human LT Antibody

To 100 μg of human LT purified by the method described in Example 12 in 0.8 ml of a physiological saline, the same volume of Freund's complete adjuvant was added and fully emulsified. The emulsion was then intraperitoneally administered to mice Balb/c (♀, n=4; 25 μg/0.4 ml/mouse), and supplemental immunization was carried out at an interval of three weeks.

Figure 8:
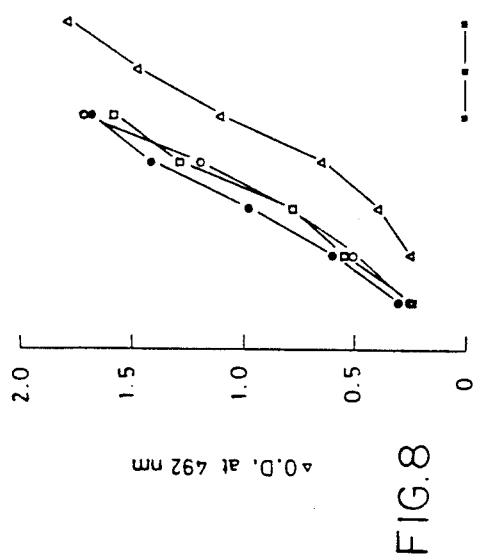
FIG. 8 is a graph showing the result obtained by measuring antibody titer in anti-LT sera by the ELISA, wherein ●, :, □ and Δ represent sera of mouse immunized by LT, and ■ represents a serum of mouse without immunization.

After the immunization was carried out three times, blood was collected from the mouse orbital plexus venosus. Serum containing anti-human LT antibodies was thus obtained. There was shown in FIG. 8 the antibody titer of the mouse serum in enzyme immunoassay wherein purified human LT described in Example 12 was used as the solid phase antigen.

Then, the neutralizing antibody titer of the antiserum to human LT was measured. In detail, to the mouse serum stepwise twice diluted, the same volume of the human LT antigen solution (2 units) was added, and the mixture was reacted for 1 hour. Thereafter, the L 929 cells were added thereto, and the conventional cytotoxicity assay described in Reference Example 1 was conducted. As the human LT antigen solution, the culture supernatant of activated lymphocytes described in Reference Example 2 and the cell extract (A) described in Example 12 were used.

Figure 9:
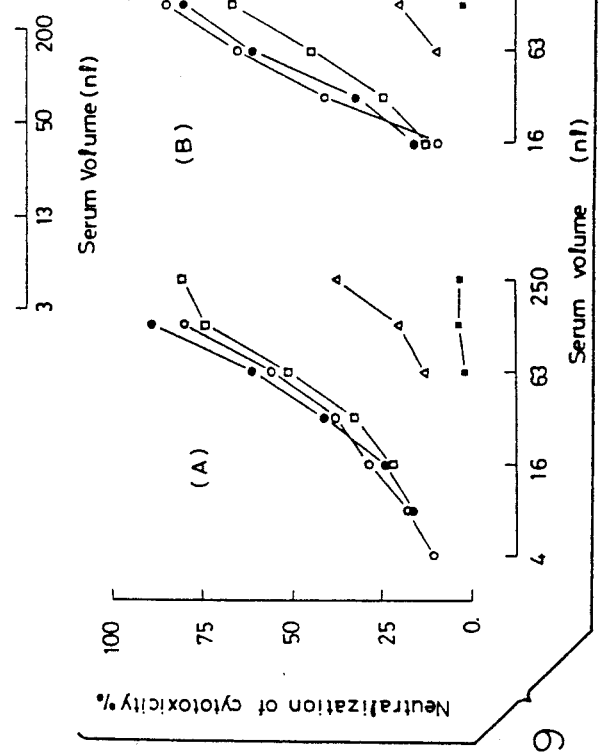
FIG. 9 indicates graphs showing the results obtained by measuring the neutralizing antibody titer of anti-LT sera, using the culture supernatant of activated lymphocytes (A) and the extract LT-expressing *E. coli* (B) as the antigen, respectively. Each of ●, :, □, Δ and ■ has the same meaning as in FIG. 8.

The results were as shown in FIG. 9. The production of neutralizing antibody against human LT was confirmed in four kinds of antisera.

The accession numbers in the deposition institutes of the strains described in the present specification, namely C600 strain, C600 strain containing plasmid pTB622 or pTB697 (E. coli C600/pTB622, E. coli 1 C600/pTB697), DH1 strain containing plasmid pTB618, pTB620, pTB848 or ptrp781 (E. coli DH1/pTB618, E. coli DH1/pTB620, E. coli DH1/pTB848, E. coli DH1/ptrp781) and AH22R⁻ strain containing plasmid pTB849 (S. cerevisiae AH22R⁻/pTB849) are as shown in Table 8.

TABLE 8

| Microorganism | IFO (IFO No.) | FERM (FERM No.) |
|---|---|---|
| E. coli C600 | 14410 | BP-808 |
| E. coli C600/pTB622 | 14544 | BP-1589 (P-9053) |
| E. coli C600/pTB697 | 14545 | BP-1590 (P-9054) |
| E. coli DH1/pTB618 | 14542 | BP-1587 (P-9051) |
| E. coli DH1/pTB620 | 14543 | BP-1588 (P-9052) |
| E. coli DH1/pTB848 | 14674 | BP-1593 |
| E. coli DH1/ptrp781 | 14546 | BP-1591 (P-9055) |
| S. cerevisiae AH22R⁻/pTB849 | 10434 | BP-1594 |

IFO: The Institute for Fermentation. Osaka, Japan.
FERM: Fermentation Research Institute, Agency of Industrial Science and Technology, Ministry of International Trade and Industry, Japan.

The following references, which are referred to for their disclosures at various points in this application, are incorporated herein by reference.

Nature 312, 721 (1984)
Nature 312, 724 (1984)
Genetic Engineering 3, 1 (1981)
Molecular cloning, A Laboratory Manual, p. 312 and p. 326 (1982)
Proc. Natl. Acad. Sci. USA, 69, 2110 (1972)
Experiments in Molecular Genetics 431–433 (1972)
Mol. Cell. Biol., 3 280 (1983)
Gene Manipulation Experimental Method (Edited by Y. Yakagi, Kodansha Japan)
Microbiol. Immunol., 28, 935 (1984)
Mol. Cell. Biol., 2 161 (1983)
Proc. Natl. Acad. Sci. USA, 72, 3961 (1975)
Nucleic Acids Res., 7 1513 (1979)
Nucleic Acids Res., 9 309 (1981)
Nucleic Acids Res., 11 3077 (1983)
Tetrahedron Lett., 21 3243 (1980)
Japanese Patent Application No. 182457/1986 (JP-A-62175182, EP-A-0225701)
Virology 52 456 (1973)
Biochem. Biophys. Res. Comm. 138 268 (1986)
J. Bacteriol. 113, 727 (1973)

We claim:

1. A polydeoxyribonucleic acid containing a nucleotide sequence coding for the following amino acid sequence or a polydeoxyribonucleic acid containing a complementary sequence thereof:

H—(Met)n—R₁—R₂—Ala—His—Ser—Thr—Leu—Lys—Pro—Ala—
Ala—His—Leu—Ile—Gly—Asp—Pro—Ser—Lys—
Gln—Asn—Ser—Leu—Leu—Trp—Arg—Ala—Asn—
Thr—Asp—Arg—Ala—Phe—Leu—Gln—Asp—Gly—
Phe—Ser—Leu—Ser—Asn—Asn—Ser—Leu—Leu—
Val—Pro—Thr—Ser—Gly—Ile—Tyr—Phe—Val—
Tyr—Ser—Gln—Val—Val—Phe—Ser—Gly—Lys—
Ala—Tyr—Ser—Pro—Lys—Ala—Thr—Ser—Ser—
Pro—Leu—Tyr—Leu—Ala—His—Glu—Val—Gln—
Leu—Phe—Ser—Ser—Gln—Tyr—Pro—Phe—His—
Val—Pro—Leu—Leu—Ser—Ser—Gln—Lys—Met—
Val—Tyr—Pro—Gly—Leu—Gln—Glu—Pro—Trp—
Leu—His—Ser—Met—Tyr—His—Gly—Ala—Ala—
Phe—Gln—Leu—Thr—Gln—Gly—Asp—Gln—Leu—
Ser—Thr—His—Thr—Asp—Gly—Ile—Pro—His—

-continued

Leu—Val—Leu—Ser—Pro—Ser—Thr—Val—Phe—
Phe—Gly—Ala—Phe—Ala—Leu—OH wherein $R_1$ is Pro or Phe, $R_2$ is a peptide chain represented by the following sequence:

Ala-Gln-Thr-Ala-Arg-Gln-His-Pro-Lys-Met-His-Leu.

or a portion thereof and n is 0 or 1.

2. The polydeoxyribonucleic acid as claimed in claim 1 wherein $R_2$ is Leu.

3. The polydeoxyribonucleic acid as claimed in claim 1, wherein $R_2$ is Ala Gln Thr Ala Arg Gln His Pro Lys Met His Leu.

4. The polydeoxyribonucleic acid as claimed in claim 2, wherein $R_1$ is Pro.

5. The polydeoxyribonucleic acid as claimed in claim 2, wherein $R_1$ is Phe.

6. The polydeoxyribonucleic acid as claimed in claim 3, wherein the codon for $R_2$ is GCT CAG ACT GCT AGA CA CAT CCT AAG ATG CAT CCT.

7. The polydeoxyribonucleic acid as claimed in claim 4, wherein the codon for $R_1$ is CCT and the codon for $R_2$ is CTT.

8. The polydeoxyribonucleic acid as claimed in claim 5, wherein the codon for $R_1$ is TTT and the codon for $R_2$ is CTT.

* * * * *